United States Patent
Kang et al.

(10) Patent No.: US 9,162,070 B2
(45) Date of Patent: Oct. 20, 2015

(54) ELECTRICAL STIMULATION SYSTEM AND CONTROL METHOD OF ELECTRICAL STIMULATION SYSTEM

(71) Applicant: Electronics and Telecommunications Research Institute, Daejeon (KR)

(72) Inventors: Mi Seon Kang, Daegu (KR); Hyun Woo Kang, Daegu (KR); Yun Su Chung, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 0 days.

(21) Appl. No.: 14/217,639

(22) Filed: Mar. 18, 2014

(65) Prior Publication Data

US 2015/0025598 A1   Jan. 22, 2015

(30) Foreign Application Priority Data

Jul. 22, 2013 (KR) ........................ 10-2013-0086081

(51) Int. Cl.
*A61N 1/00* (2006.01)
*A61N 1/372* (2006.01)
*A61N 1/36* (2006.01)

(52) U.S. Cl.
CPC ........ *A61N 1/37252* (2013.01); *A61N 1/36135* (2013.01); *A61N 1/36132* (2013.01)

(58) Field of Classification Search
CPC ........... A61N 1/36135; A61N 1/36139; A61N 1/36132; A61N 2001/34; A61N 1/36014; A61N 1/36021; A61N 2/004; A61B 5/4824; A61B 5/4827
See application file for complete search history.

(56) References Cited

U.S. PATENT DOCUMENTS

2013/0053722 A1* 2/2013 Carlson et al. ................ 600/554
2014/0257438 A1* 9/2014 Simon et al. .................... 607/72

FOREIGN PATENT DOCUMENTS

KR   10-2006-0002384   1/2006
KR   10-2009-0124462   12/2009

* cited by examiner

*Primary Examiner* — Robert N Wieland
(74) *Attorney, Agent, or Firm* — Kile Park Reed & Houtteman PLLC

(57) ABSTRACT

Provided is an electrical system including an intelligent learning terminal to analyze biometric information associated with a user and calculate an intensity of electrical stimulation for the user based on a result of the analyzing, and at least one wireless electrical stimulator to provide electrical stimulation to the user based on the calculated intensity of electrical stimulation, wherein the intelligent learning terminal is connected to the at least one wireless electrical stimulator based on wired or wireless communication.

20 Claims, 10 Drawing Sheets

FIG. 3

| WIRELESS ELECTRICAL STIMULATOR 1 | WIRELESS ELECTRICAL STIMULATOR 2 | WIRELESS ELECTRICAL STIMULATOR 3 | WIRELESS ELECTRICAL STIMULATOR 1 |
|---|---|---|---|
| GENDER: | GENDER: | GENDER: | WIRELESS ELECTRICAL STIMULATOR 2 |
| AGE: | AGE: | AGE: | WIRELESS ELECTRICAL STIMULATOR 3 |
| BIOMETRIC INFORMATION: | BIOMETRIC INFORMATION: | BIOMETRIC INFORMATION: | WIRELESS ELECTRICAL STIMULATOR 4 |
| STIMULATION INTENSITY: | STIMULATION INTENSITY: | STIMULATION INTENSITY: | WIRELESS ELECTRICAL STIMULATOR 5 |
| REMAINING TIME: | REMAINING TIME: | REMAINING TIME: | WIRELESS ELECTRICAL STIMULATOR 6 |

FIG. 5

```
┌─────────────────────┐
│ WIRELESS ELECTRICAL │
│    STIMULATOR #     │
├─────────────────────┤
│                     │
│ GENDER:             │
│                     │
│ AGE:                │
│                     │
│ BIOMETRIC           │
│ INFORMATION:        │
│                     │
│ STIMULATION         │
│ INTENSITY:          │
│                     │
│ REMAINING TIME:     │
│                     │
└─────────────────────┘
```

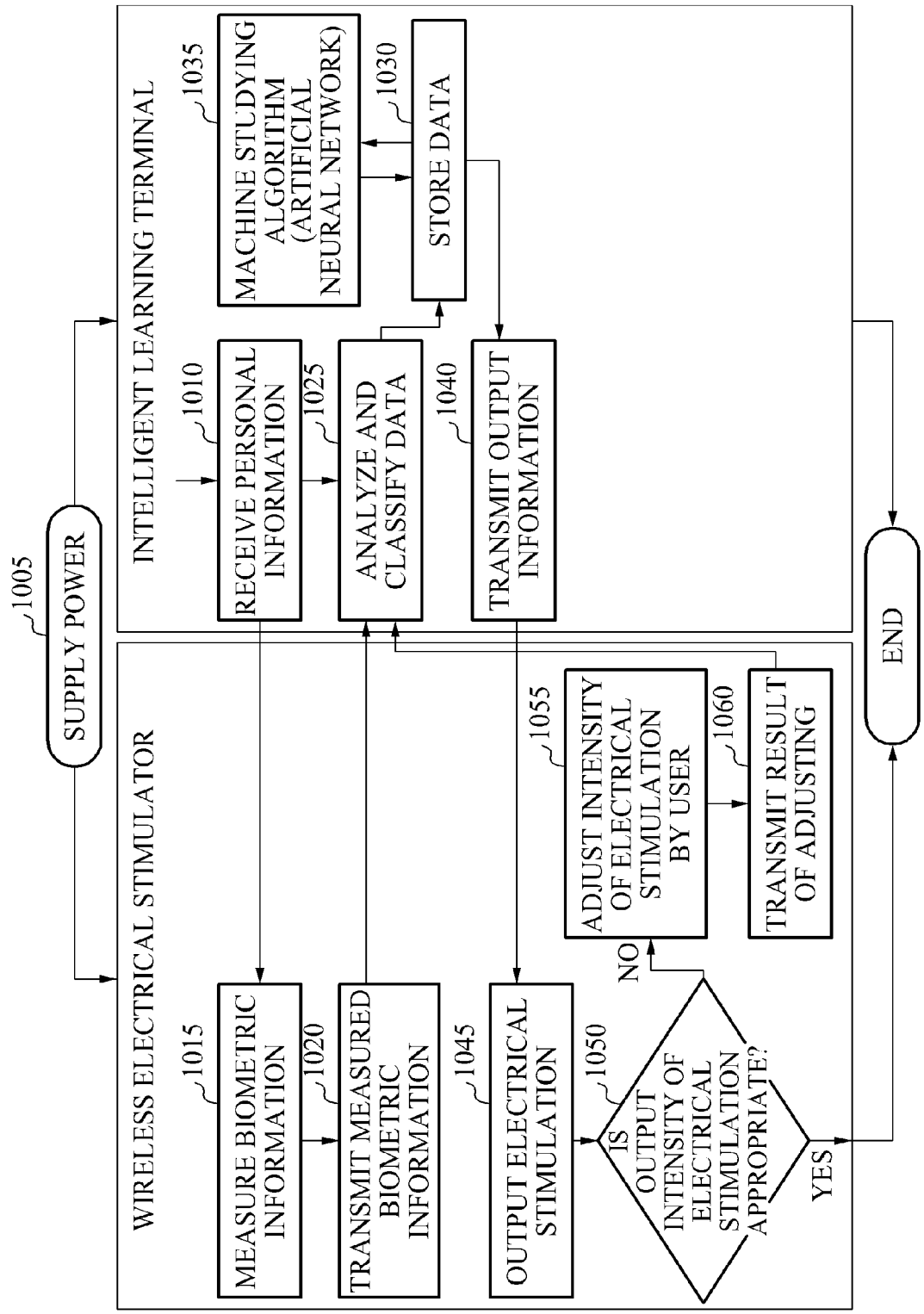

ELECTRICAL STIMULATION SYSTEM AND CONTROL METHOD OF ELECTRICAL STIMULATION SYSTEM

CROSS-REFERENCE TO RELATED APPLICATION

This application claims the priority benefit of Korean Patent Application No. 10-2013-0086081, filed on Jul. 22, 2013, in the Korean Intellectual Property Office, the disclosure of which is incorporated herein by reference.

BACKGROUND

1. Field of the Invention

The present invention relates to an electrical stimulation system including an intelligent learning terminal connected to at least one wireless electrical stimulator based on wired or wireless communication, and a control method of the electrical stimulation system.

2. Description of the Related Art

A body has characteristics of generating an infinitesimal amount of electricity and sensitively changing in response to electrical stimulation provided from an external source. Recently, due to an increased public interest in alleviating chronic pain, treatment devices based on such characteristics of the body have been developed.

However, an effectiveness of such treatment devices may be maximized for predetermined body parts having a high frequency of usage, for example, a shoulder, a waist, an abdomen, arms, legs, and the like. In addition, a user may face an inconvenience of adjusting an intensity of electrical stimulation each time a treatment device is used. Also, a degree of difficulty in manipulation of the treatment devices may result due to a physical disability resulting from application of an inappropriate intensity of electrical stimulation.

In a case of devices designed for use in a hospital setting, since adjustment of an intensity of electrical stimulation is performed by a doctor or a physiotherapist while listening to feedback from a patient, a substantial amount of time and human resources may be required. From the perspective of a patient, placing the responsibility of making direct, suitable adjustments to an intensity of electrical stimulation on the patient may be inconvenient. Also, providing an appropriate intensity of electrical stimulation to a patient experiencing communication difficulties may be complicated.

SUMMARY

An aspect of the present invention provides an appropriate intensity of electrical stimulation to a user by collecting and analyzing biometric information associated with the user using at least one sensor.

Another aspect of the present invention also provides an appropriate intensity of electrical stimulation to a user such as a patient with a physical difficulty, based on biometric information by enabling the user to directly adjust the intensity of electrical stimulation.

According to an aspect of the present invention, there is provided an electrical system including an intelligent learning terminal to analyze biometric information associated with a user and calculate an intensity of electrical stimulation for the user based on a result of the analyzing, and at least one wireless electrical stimulator to provide electrical stimulation to the user based on the calculated intensity of electrical stimulation, wherein the intelligent learning terminal is connected to the at least one wireless electrical stimulator based on wired or wireless communication.

The intelligent learning terminal may classify the result of the analyzing for each user and store the classified result.

The intelligent learning terminal may receive an intensity of electrical stimulation set by the user as feedback, and learn the intensity of electrical stimulation set by the user and the calculated intensity of electrical stimulation.

The intelligent learning terminal may store the intensity of electrical stimulation set by the user.

The intelligent learning terminal may adjust a preset intensity of electrical stimulation based on the intensity of electrical stimulation set by the user, and learn the adjusted intensity of electrical stimulation.

The intelligent learning terminal may recognize the user based on the result of the analyzing of biometric information associated with the user.

The intelligent learning terminal may include an adjustment unit to receive personal information associated with the user and adjust a state of a connection between the intelligent learning terminal and the at least one wireless electrical stimulator, and a liquid crystal display (LCD) unit to display at least one of information associated with the at least one wireless electrical stimulator connected to the intelligent learning terminal, personal information associated with the user, and information input by the adjustment unit.

The at least one wireless electrical stimulator may include at least one sensor to sense a biometric signal of the user, and collect biometric information associated with the user sensed using the at least one sensor.

The at least one wireless electrical stimulator may include a wireless communication module to transmit the collected biometric information to the intelligent learning terminal based on the wired or wireless communication, and an electrical stimulation output unit to provide electrical stimulation to the user based on the calculated intensity of electrical stimulation.

The at least one wireless electrical stimulator may include an adjustment unit to receive an intensity of electrical stimulation and a time set by the user, and adjust an intensity of electrical stimulation and a time output by the electrical stimulation output unit based on the intensity of electrical stimulation and the time set by the user, and an LCD unit to display the intensity of electrical stimulation set by the user and a remaining time.

The at least one wireless electrical stimulator may operate in response to a control signal of the intelligent learning terminal.

According to another aspect of the present invention, there is also provided a control method of an electrical stimulation system including an intelligent learning terminal and at least one wireless electrical stimulator, the method including collecting biometric information associated with a user using the at least one wireless electrical stimulator, analyzing the collected biometric information, calculating an intensity of electrical stimulation for the user based on a result of the analyzing, and providing electrical stimulation to the user based on the calculated intensity of electrical stimulation.

The control method may further include verifying a state of a connection between the intelligent learning terminal and the at least one wireless electrical stimulator when a power is supplied.

The collecting may include receiving personal information associated with the user from the intelligent learning terminal, measuring a biometric signal of the user using the at least one wireless electrical stimulator based on a result of the receiving, and collecting a result of the measuring.

The control method may further include classifying the result of the analyzing for each user and storing the classified result.

The control method may further include receiving an intensity of electrical stimulation set by the user as feedback, and learning the intensity of electrical stimulation set by the user and the calculated intensity of electrical stimulation.

The control method may further include storing the intensity of electrical stimulation set by the user.

The control method may further include adjusting a preset intensity of electrical stimulation, based on the intensity of electrical stimulation set by the user, storing the adjusted intensity of electrical stimulation, and learning the adjusted intensity of electrical stimulation.

The control method may further include recognizing the user based on the result of the analyzing of biometric information associated with the user.

The control method may further include receiving an intensity of electrical stimulation and a time set by the user, and adjusting an intensity of electrical stimulation and a time output by the at least one wireless electrical stimulator based on the intensity of electrical stimulation and the time set by the user.

BRIEF DESCRIPTION OF THE DRAWINGS

These and/or other aspects, features, and advantages of the invention will become apparent and more readily appreciated from the following description of exemplary embodiments, taken in conjunction with the accompanying drawings of which:

FIG. 3 is a diagram illustrating a display displayed on a liquid crystal display (LCD) unit of the intelligent learning terminal of FIG. 2;

FIG. 5 is a diagram illustrating a display displayed on an LCD unit of the wireless electrical stimulator of FIG. 4;

FIG. 10 is a diagram illustrating an operation of an electrical stimulation system according to an example embodiment.

DETAILED DESCRIPTION

Figure 1:
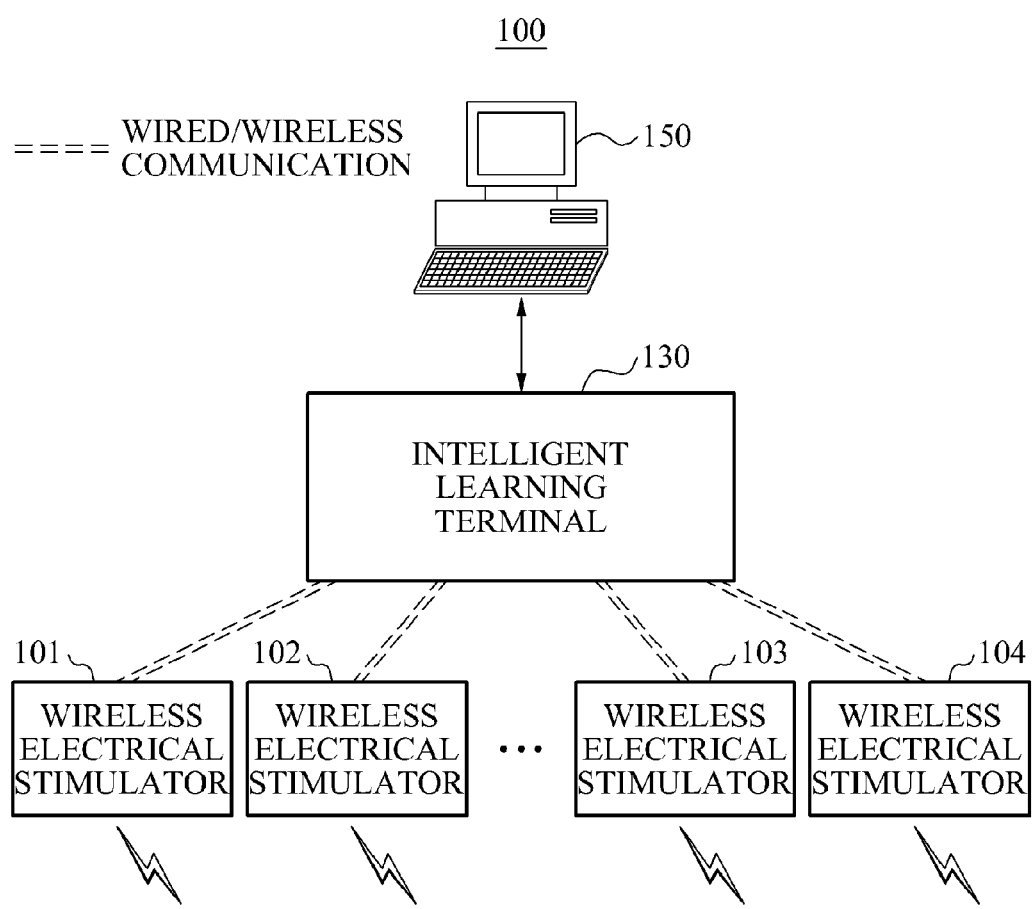
FIG. 1 is a diagram illustrating a configuration of an electrical stimulation system according to an example embodiment.

Reference will now be made in detail to exemplary embodiments of the present invention, examples of which are illustrated in the accompanying drawings, wherein like reference numerals refer to the like elements throughout. Exemplary embodiments are described below to explain the present invention by referring to the figures.

FIG. 1 is a diagram illustrating a configuration of an electrical stimulation system 100 according to an example embodiment.

Referring to FIG. 1, the electrical stimulation system 100 may include wireless electrical stimulators 101, 102, 103, and 104, and an intelligent learning terminal 130.

The intelligent learning terminal 130 may be connected to each of the wireless electrical stimulators 101, 102, 103, and 104 using wired or wireless communication. Each of the wireless electrical stimulators 101, 102, 103, and 104 may communicate with the intelligent learning terminal 130, and the wireless electrical stimulators 101, 102, 103, and 104 may not communicate with each other.

The intelligent learning terminal 130 may control the wireless electrical stimulators 101, 102, 103, and 104. For example, each of the wireless electrical stimulators 101, 102, 103, and 104 may operate in response to a control signal of the intelligent learning terminal 130 being received. When the control signal is received, each of the wireless electrical stimulators 101, 102, 103, and 104 in a standby mode may operate in response to the control signal.

The respective wireless electrical stimulators 101, 102, 103, and 104 may be used for each user through being attached to a desired part of a body of each user.

The intelligent learning terminal 130 may be connected to a computer 150 using wired communication. The user may verify or control information included in the intelligent learning terminal 130 using the computer, as necessary.

Figure 2:
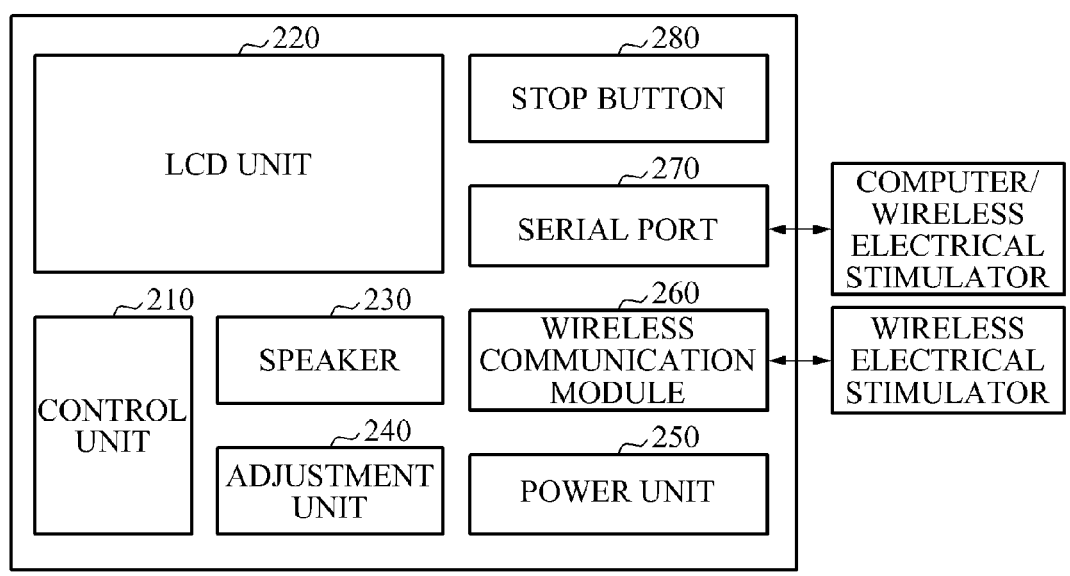
FIG. 2 is a block diagram illustrating an intelligent learning terminal according to an example embodiment.

FIG. 2 is a block diagram illustrating an intelligent learning terminal 200 according to an example embodiment.

Referring to FIG. 2, the intelligent learning terminal 200 may include a control unit 210, a liquid crystal display (LCD) unit 220, a speaker 230, an adjustment unit 240, a power unit 250, a wireless communication module 260, a serial port 270, and a stop button 280.

The control unit 210 may analyze biometric information associated with a user, and calculate an intensity of electrical stimulation for the user based on a result of the analyzing. The control unit 210 may classify the result of the analyzing of the biometric information for each user and store the classified result.

The control unit 210 may receive an intensity of electrical stimulation feed back from the user, and learn the intensity of electrical stimulation feed back from the user and the calculated intensity of electrical stimulation. Also, the control unit 210 may adjust a predetermined intensity of electrical stimulation based on the intensity of electrical stimulation feed back from the user, and learn the adjusted intensity of electrical stimulation.

The control unit 210 may recognize the user based on the result of the analyzing of the biometric information associated with the user. The control unit 210 may match the recognized user and personal information associated with the corresponding user so as to store or learn an intensity of electrical stimulation to be calculated, or an intensity of electrical stimulation to be subsequently feed back.

The adjustment unit 240 may adjust a state of a connection between at least one wireless electrical stimulator and the intelligent learning terminal 200, and receive personal information including, for example, an age and a gender of a user using the at least one wireless electrical stimulator.

The LCD unit 220 may display at least one of information associated with the at least one wireless electrical terminal connected to the intelligent learning terminal 200, personal information associated with a user, and information input by the adjustment unit 240.

The power unit 250 may provide a direct supply of power for operating the intelligent learning terminal 200, or provide a power supplied from an external source to the intelligent learning terminal 200.

The intelligent learning terminal 200 may be connected to the at least one wireless electrical stimulator and the computer 150 using the serial port 270. When the intelligent learning terminal 200 is connected to the at least one wireless electrical stimulator using wired communication, the intelligent learning terminal 200 may be connected to the at least one wireless electrical stimulator using the serial port 270.

When the intelligent learning terminal 200 is connected to the at least one wireless electrical stimulator using wired communication, the intelligent learning terminal 200 may be connected to the at least one wireless electrical stimulator using the wireless communication module 260.

When a period of time during which the at least one wireless electrical stimulator is used ends, an alarm may sound, and the alarm may be transferred using the speaker 230. When an improper operation occurs in the intelligent learning terminal 200 or the at least one wireless electrical stimulator, the alarm may sound using the speaker 230 in order to provide a notification indicating an occurrence of the improper operation. When the alarm sounds, the user may use the stop button 280 in order to simultaneously halt operations of all wireless electrical stimulators connected to the intelligent learning terminal 200 using wired or wireless communication.

FIG. 3 is a diagram illustrating a display displayed on the LCD unit 220 of the intelligent learning terminal 200 of FIG. 2.

Referring to FIG. 3, the LCD unit 220 of the intelligent learning terminal 200 may display information included in a wireless electrical stimulator currently connected to the intelligent learning terminal 200.

The LCD unit 220 may display personal information, for example an age and a gender of a user, input by the intelligent learning terminal 200, biometric information transferred by a wireless electrical stimulator being used by a corresponding user, and information including a remaining time and an intensity of electrical stimulation provided to the user by the wireless electrical stimulator, and the like. Also, the LCD unit 220 may display information associated with all wireless electrical stimulators.

Figure 4:
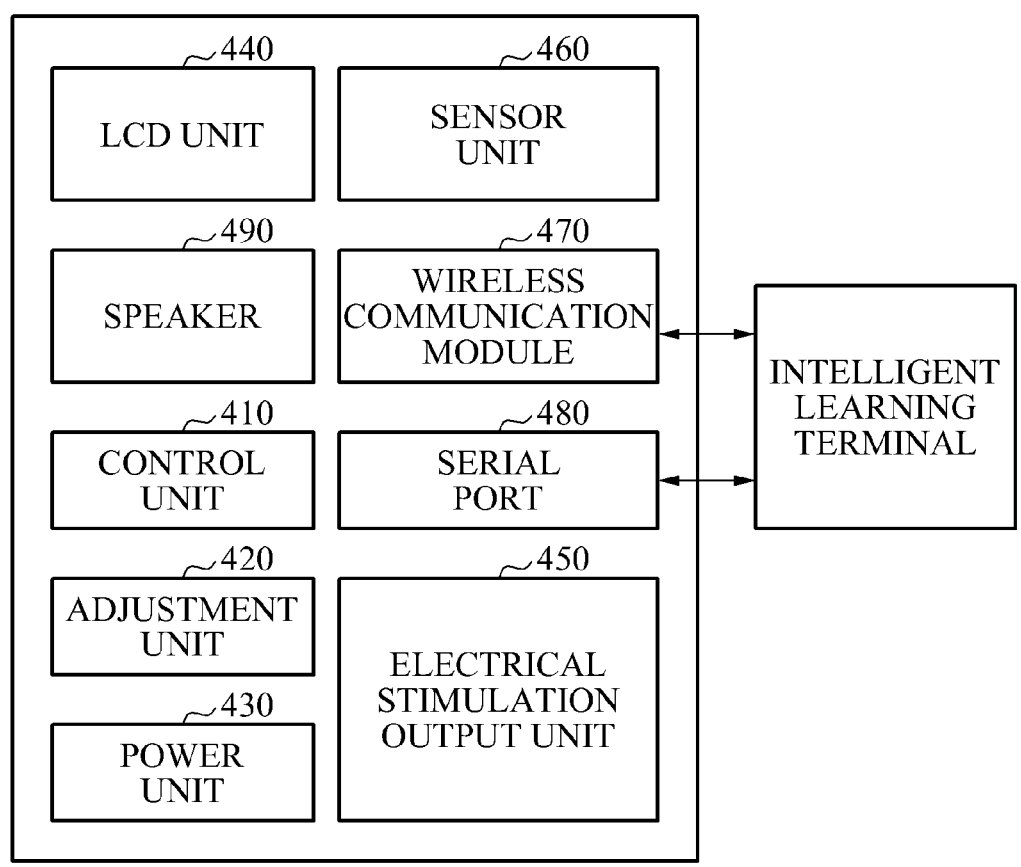
FIG. 4 is a block diagram illustrating a wireless electrical stimulator according to an example embodiment.

FIG. 4 is a block diagram illustrating a wireless electrical stimulator 400 according to an example embodiment.

Referring to FIG. 4, the wireless electrical stimulator 400 may include a control unit 410, an adjustment unit 420, a power unit 430, an LCD unit 440, an electrical stimulation output unit 450, a sensor unit 460, a wireless communication module 470, a serial port 480, and a speaker 490.

The wireless electrical stimulator 400 may be connected to the intelligent learning terminal 130 of FIG. 1 using wired or wireless communication, and operate in response to a control signal of the intelligent learning terminal 130 being received.

The control unit 410 may provide electrical stimulation to a user based on an intensity of electrical stimulation calculated by the intelligent learning terminal 130.

The adjustment unit 420 may receive an intensity of electrical stimulation and a time set by the user, and adjust an intensity of electrical stimulation and a time output by the electrical stimulation output unit 450 based on the intensity of electrical stimulation and a time set by the user. The user may adjust an intensity of electrical stimulation and a time for receiving electrical stimulation suitable for the user.

The power unit 430 may supply power for generating an electrical stimulation output by the electrical stimulation output unit 450.

The LCD unit 440 may display the remaining time and the intensity of electrical stimulation set by the user.

The electrical stimulation output unit 450 may refer to a portion for providing electrical stimulation to the user, and provide the electrical stimulation to the user based on the intensity of electrical stimulation calculated by the intelligent learning terminal 130.

The sensor unit 460 may include at least one sensor to sense a biometric signal of the user, and sense the biometric signal, for example, a temperature, a pulse, a skin resistance of the user using the at least one sensor.

The wireless electrical stimulator 400 may collect biometric information sensed by the sensor unit 460, and transmit the collected biometric information to the intelligent learning terminal 130 using the wireless communication module 470.

When the wireless electrical stimulator 400 is connected to the intelligent learning terminal 130 using wireless communication, the wireless electrical stimulator 400 may be connected to the intelligent learning terminal 130 using the wireless communication module 470.

When the wireless electrical stimulator 400 is connected to the intelligent learning terminal 130 using wired communication, the wireless electrical stimulator 400 may be connected to the intelligent learning terminal 130 using the serial port 480.

The speaker 490 may sound an alarm when an operation time of the wireless electrical stimulator 400 ends.

FIG. 5 is a diagram illustrating a display displayed on the LCD unit 440 of the wireless electrical stimulator 400 of FIG. 4.

Referring to FIG. 5, the LCD unit 440 may display personal information, for example, an age and a gender of a user, input by the wireless electrical stimulator 400, biometric information sensed by a corresponding wireless electrical stimulator, and information including a remaining time and an intensity of electrical stimulator being provided to the user on the display.

Figure 6:
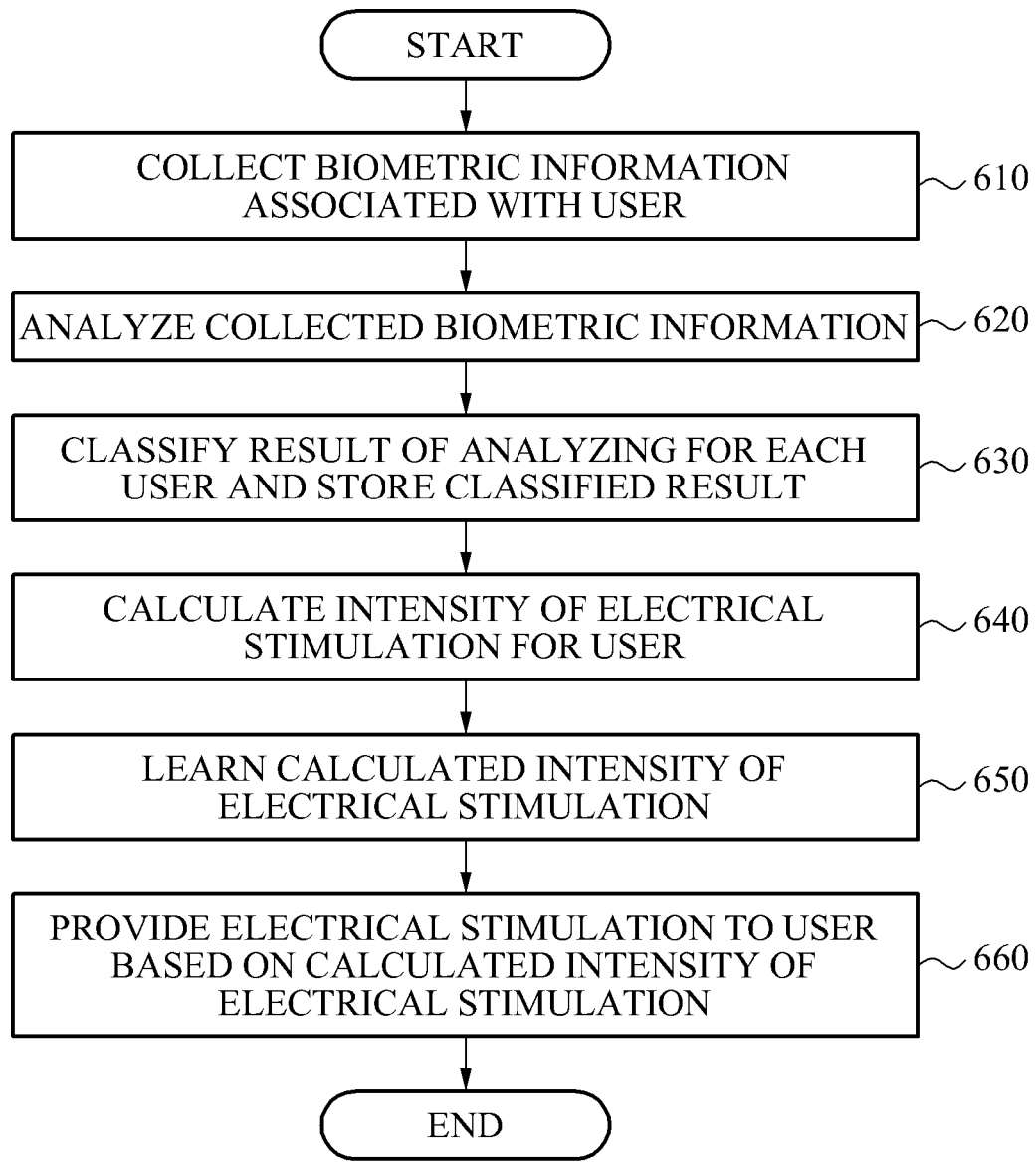
FIG. 6 is a flowchart illustrating a control method of an electrical stimulation system according to an example embodiment.

FIG. 6 is a flowchart illustrating a control method of an electrical stimulation system according to an example embodiment.

Referring to FIG. 6, in operation 610, the electrical stimulation system including at least one wireless electrical stimulator and an intelligent learning terminal according to an example embodiment may collect biometric information associated with a user using the at least one wireless electrical stimulator. Descriptions about the method of collecting a biometric signal associated with a user in the electrical stimulation system will be provided with reference to FIG. 7.

In operation 620, the electrical stimulation system may analyze the collected biometric information.

In operation 630, the electrical stimulation system may classify a result of the analyzing for each user and store the classified result.

In this instance, an execution order of operation 630 is not intended to be limited to example embodiments provided herein, and may be performed in various manners. Depending on an example embodiment, operation 630 may be performed after operation 640 or operation 660 ends.

In operation 640, the electrical stimulation system may calculate an intensity of electrical stimulation for the user based on the result of the analyzing of operation 620.

In operation 650, the electrical stimulation system may match the intensity of electrical stimulation calculated in operation 640 and a corresponding user, and learn a result of the matching.

In operation 660, the electrical stimulation system may provide an appropriate intensity of electrical stimulation to the user based on the intensity of electrical stimulation calculated in operation 640.

For example, when five users including A, B, C, D, and E use the electrical stimulation system, and each of the five users use one wireless electrical stimulator, biometric information associated with the five users may be transferred from the five wireless electrical stimulators to the intelligent learning terminal.

The electrical stimulation system may analyze the collected biometric information associated with the five users, and classify a result of the analyzing for each of the five users including A, B, C, D, and E, thereby storing the classified result of the analyzing.

The electrical stimulation system may calculate an intensity of electrical stimulation for each user based on the result of the analyzing, and provide the calculated intensity of electrical stimulation to be suitable for each user. In this instance, the calculated intensity of electrical stimulation may be matched to each user in order to be learned. The intensity of electrical stimulation for each user may be continuously learned in the intelligent learning terminal in addition to an intensity of electrical stimulation fed back based on a control of the user.

The intensity of electrical stimulation may be provided for each user through the wireless electrical stimulator being used by the corresponding user, and the intensity of electrical stimulation for each user may be provided for each user concurrently, or at different times.

Figure 7:
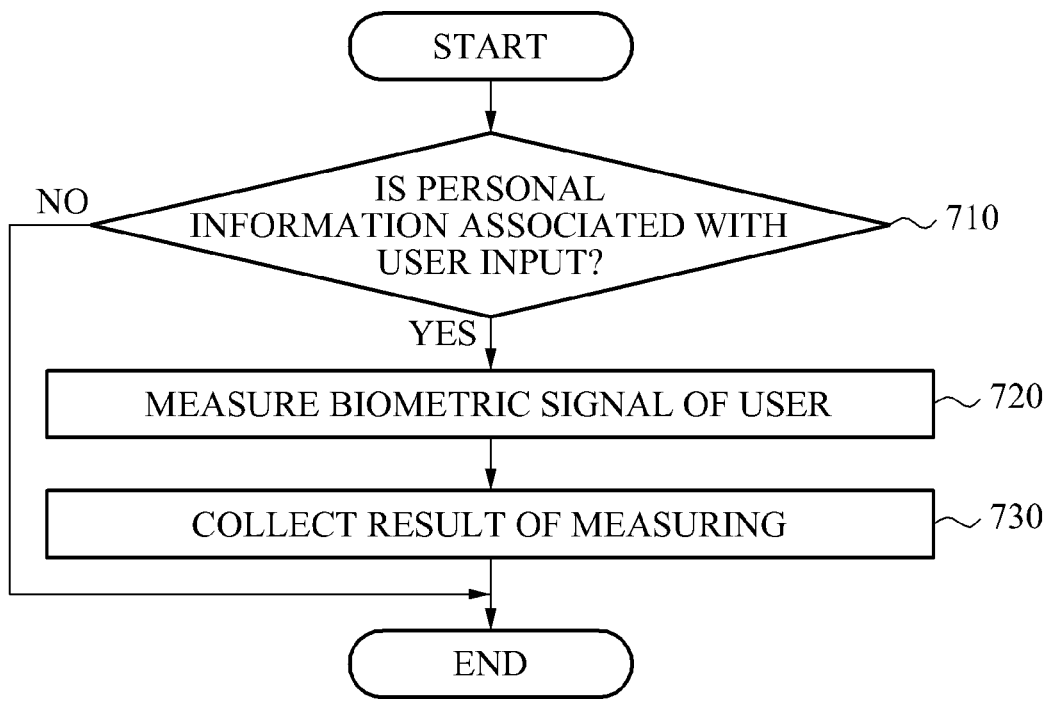
FIG. 7 is a flowchart illustrating a method of collecting biometric information associated with a user of the electrical stimulation system of FIG. 6.

FIG. 7 is a flowchart illustrating a method of collecting biometric information associated with a user of the electrical stimulation system of FIG. 6.

Referring to FIG. 7, in operation 710, an electrical stimulation system according to an example embodiment may determine whether personal information associated with the user is input from an intelligent learning terminal.

When the personal information associated with the user is not determined to be input in operation 710, the electrical stimulation system may terminate an operation.

In operation 720, when the personal information associated with the user is determined to be input in operation 710, the electrical stimulation system may measure a biometric signal of the user using at least one wireless electrical stimulator.

In operation 730, the electrical stimulation system may collect a result of the measuring.

Figure 8:
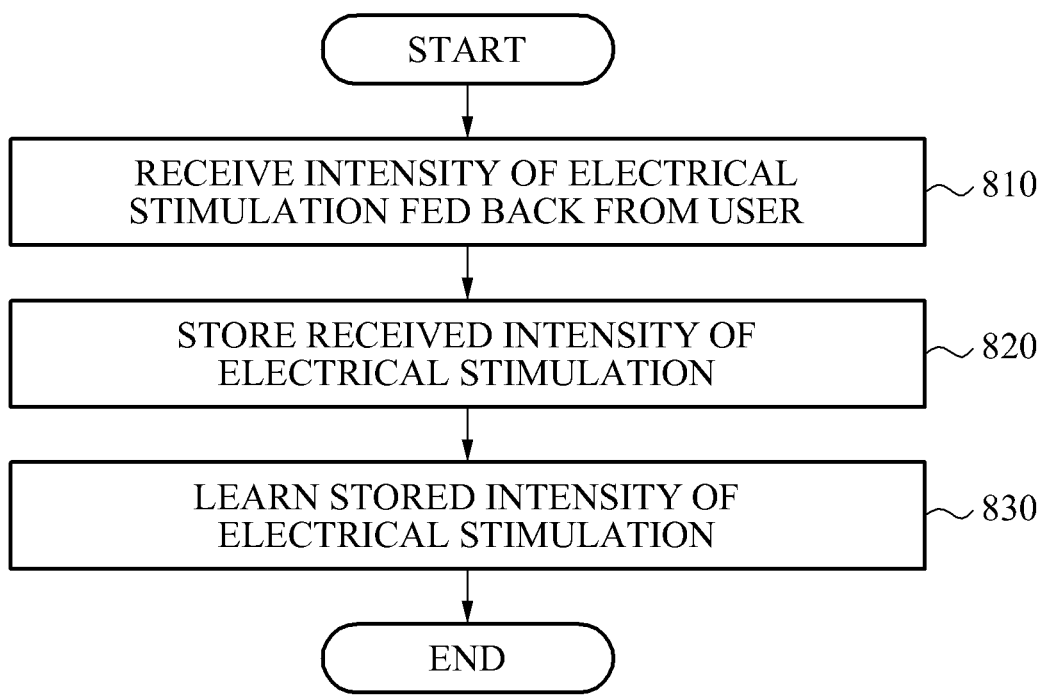
FIG. 8 is a flowchart illustrating a control method of an electrical stimulation system according to another example embodiment.

FIG. 8 is a flowchart illustrating a control method of an electrical stimulation system according to another example embodiment.

Referring to FIG. 8, the electrical stimulation system may learn an intensity of electrical stimulation based on an intensity of electrical stimulation fed back from a user.

In operation 810, the electrical stimulation system may receive the intensity of electrical stimulation fed back from the user.

In operation 810, the intensity of electrical stimulation fed back from the user may be an intensity of electrical stimulation output from a wireless stimulator based on an intensity of electrical stimulation set or adjusted by the user.

In operation 820, the electrical stimulation system may store the intensity of electrical stimulation received in operation 810. In operation 830, the electrical stimulation system may learn the stored intensity of electrical stimulation in addition to a previously stored intensity of electrical stimulation.

Figure 9:
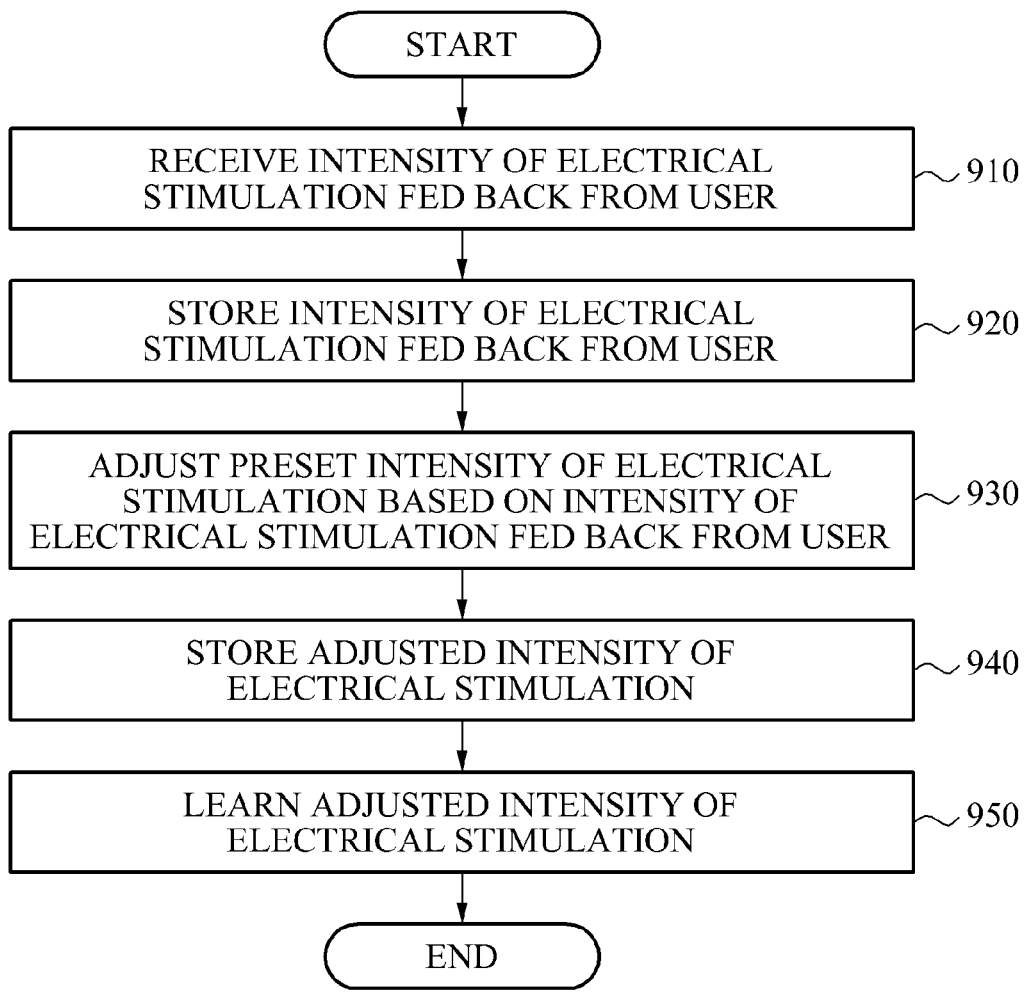
FIG. 9 is a flowchart illustrating a control method of an electrical stimulation system according to still another example embodiment.

FIG. 9 is a flowchart illustrating a control method of an electrical stimulation system according to still another example embodiment.

Referring to FIG. 9, the electrical stimulation system may learn an intensity of electrical stimulation based on an intensity of electrical stimulation fed back from a user.

In operation 910, the electrical stimulation system may receive the intensity of electrical stimulation fed back from the user. In operation 920, the electrical stimulation system may store the received intensity of electrical stimulation.

In operation 930, the electrical stimulation system may adjust a preset intensity of electrical stimulation based on the intensity of electrical stimulation fed back from a user.

In operation 940, the electrical stimulation system may store the adjusted intensity of electrical stimulation. In operation 950, the electrical stimulation system may learn the stored intensity of electrical stimulation in addition to a previously stored intensity of electrical stimulation.

FIG. 10 is a diagram illustrating an operation of an electrical stimulation system according to an example embodiment.

Referring to FIG. 10, in operation 1005, when a power is supplied to the electrical stimulation system according to an example embodiment, an intelligent learning terminal may verify a state of a connection to a wireless electrical stimulator.

In operation 1010, when the intelligent learning terminal is verified to be connected to the wireless electrical stimulator, the intelligent learning terminal may receive personal information such as an age and a gender of a user, and transmit the personal information to the wireless electrical stimulator.

In operation 1015, when the wireless electrical stimulator receives the personal information from the intelligent learning terminal, the wireless electrical stimulator may measure biometric information associated with the user using a sensor. In operation 1020, the wireless electrical stimulator may transmit a result of the measuring, for example, sensor information to the intelligent learning terminal.

In operation 1025, the intelligent learning terminal may analyze the result of the measuring, for example, sensor information received in operation 1020, and classify the result of the analyzing for each user. In operation 1030, the intelligent learning terminal may store the classified result.

In operation 1035, the intelligent learning terminal may calculate an intensity of electrical stimulation suitable for the user, using a machine studying algorithm based on information stored in operation 1030. In operation 1030, the intelligent learning terminal may store the calculated intensity of electrical stimulation. Simultaneously, in operation 1040, the intelligent learning terminal may transmit the classified result as output information.

In operation 1045, the wireless electrical stimulator may output electrical stimulation to the user based on the output information received from operation 1040. In operation 1050, the wireless electrical stimulator may determine whether an intensity of the electrical stimulation output in operation 1045 is appropriate.

In operation 1050, the determining of whether the intensity of the electrical stimulation output in operation 1045 is appropriate may be performed based on whether the user adjusts the intensity of electrical stimulation while the electrical stimulation is being provided.

In operation 1050, when the user does not adjust the intensity of electrical stimulation of the wireless electrical stimulator, the intensity of the electrical stimulation output may be determined to be appropriate. When the intensity of the electrical stimulation is appropriate, the wireless electrical stimulator may provide the electrical stimulation during a predetermined period, and terminate an operation without providing feedback on the intensity of electrical stimulation.

In operation 1055, when the user adjusts the intensity of electrical stimulation in operation 1050, the electrical stimulation system may determine that the intensity of the electrical stimulation being provided to the user is inappropriate or causes an inconvenience. When the intensity of the electrical stimulation being provided to the user is inappropriate or causes an inconvenience, the user may adjust the intensity of the electrical stimulation to be suitable for the user using an adjustment unit.

In operation 1060, when the intensity of electrical stimulation is adjusted, the wireless electrical stimulator may transmit or feedback the adjusted intensity of electrical stimulation to the intelligent learning terminal.

In operation 1025, the intelligent learning terminal may analyze and classify information transmitted from operation 1060 so as to be stored as data in operation 1030. The electrical stimulation system may apply the machine learning algorithm to the data stored in operation 1030, thereby providing appropriate output information to the user.

In an example embodiment, the intelligent learning terminal may continuously store and analyze the intensity of electrical for the user, and learn a result of the analyzing to provide an intensity of electrical suitable for the user. The machine learning algorithm may be used in a process of the learning.

The intelligent learning terminal may acquire an optimal intensity of electrical stimulation for each user through continuous learning based on the machine learning algorithm. The optimal intensity of electrical stimulation for each user acquired through continuous learning may be stored in a memory or a cache.

Accordingly, the user may be provided with the optimal intensity of electrical stimulation without needing to be adjusted each time the electrical stimulation system is used. When the continuous leaning of an intensity of electrical stimulation suitable for each user is performed, a patient experiencing difficulty in moving may be provided a suitable intensity of electrical stimulation based on a result of the learning without inconvenience resulting from a need to constantly adjust an intensity of electrical stimulation.

According to an aspect of the present invention, it is possible for an electrical stimulator to provide an appropriate intensity of electrical stimulation to a user based on biometric information associated with the user.

According to another aspect of the present invention, it is possible for a user to directly adjust an intensity of electrical stimulation to be suitable for the user, and provide an appropriate intensity of electrical stimulation to a patient experiencing communication difficulties.

According to still another aspect of the present invention, it is possible to provide electrical stimulation to a plurality of patients, concurrently.

The methods according to the above-described embodiments may be recorded, stored, or fixed in one or more non-transitory computer-readable media that includes program instructions to be implemented by a computer to cause a processor to execute or perform the program instructions. The media may also include, alone or in combination with the program instructions, data files, data structures, and the like. The program instructions recorded on the media may be those specially designed and constructed, or they may be of the kind well-known and available to those having skill in the computer software arts. Examples of non-transitory computer-readable media include magnetic media such as hard disks, floppy disks, and magnetic tape; optical media such as CD ROM discs and DVDs; magneto-optical media such as optical discs; and hardware devices that are specially configured to store and perform program instructions, such as read-only memory (ROM), random access memory (RAM), flash memory, and the like. Examples of program instructions include both machine code, such as produced by a compiler, and files containing higher level code that may be executed by the computer using an interpreter. The described hardware devices may be configured to act as one or more software modules in order to perform the operations and methods described above, or vice versa.

Although a few embodiments of the present invention have been shown and described, the present invention is not limited to the described embodiments. Instead, it would be appreciated by those skilled in the art that changes may be made to these embodiments without departing from the principles and spirit of the invention, the scope of which is defined by the claims and their equivalents.

What is claimed is:

1. An electrical system comprising:
   an intelligent learning terminal to analyze biometric information associated with a user and calculate an intensity of electrical stimulation for the user based on a result of the analyzing; and
   at least one wireless electrical stimulator to provide electrical stimulation to the user based on the calculated intensity of electrical stimulation,
   wherein the intelligent learning terminal is connected to the at least one wireless electrical stimulator based on wired or wireless communication, and learns the calculated intensity of electrical stimulation by matching the calculated intensity of electrical stimulation with the user.

2. The system of claim 1, wherein the intelligent learning terminal classifies the result of the analyzing for each user and stores the classified result.

3. The system of claim 1, wherein the intelligent learning terminal receives an intensity of electrical stimulation set by the user as feedback, and learns the intensity of electrical stimulation set by the user by matching the intensity of electric stimulation set by the user.

4. The system of claim 3, wherein the intelligent learning terminal stores the intensity of electrical stimulation set by the user.

5. The system of claim 1, wherein the intelligent learning terminal receives an intensity of electrical stimulation set by the user as feedback, stores the intensity of electrical stimulation set by the user, adjusts a preset intensity of electrical stimulation based on the intensity of electrical stimulation set by the user, and learns the adjusted intensity of electrical stimulation by matching the adjusted intensity of electrical stimulation with the user.

6. The system of claim 1, wherein the intelligent learning terminal recognizes the user based on the result of the analyzing of biometric information associated with the user.

7. The system of claim 1, wherein the intelligent learning terminal comprises:
   an adjustment unit to receive personal information associated with the user and adjust a state of a connection between the intelligent learning terminal and the at least one wireless electrical stimulator; and
   a liquid crystal display unit to display at least one of information associated with the at least one wireless electrical stimulator connected to the intelligent learning terminal, personal information associated with the user, and information input by the adjustment unit.

8. The system of claim 1, wherein the at least one wireless electrical stimulator comprises at least one sensor to sense a biometric signal of the user, and collects biometric information associated with the user sensed using the at least one sensor.

9. The system of claim 8, wherein the at least one wireless electrical stimulator comprises:
a wireless communication module to transmit the collected biometric information to the intelligent learning terminal based on the wired or wireless communication; and
an electrical stimulation output unit to provide electrical stimulation to the user based on the calculated intensity of electrical stimulation.

10. The system of claim 9, wherein the at least one wireless electrical stimulator comprises:
an adjustment unit to receive an intensity of electrical stimulation and a time set by the user, and adjust an intensity of electrical stimulation and a time output by the electrical stimulation output unit based on the intensity of electrical stimulation and the time set by the user; and
a liquid crystal display unit to display the intensity of electrical stimulation set by the user and a remaining time.

11. The system of claim 1, wherein the at least one wireless electrical stimulator operates in response to a control signal of the intelligent learning terminal.

12. A control method of an electrical stimulation system comprising an intelligent learning terminal and at least one wireless electrical stimulator for at least one user, the method comprising:
collecting biometric information associated with a user using the at least one wireless electrical stimulator;
analyzing the collected biometric information;
calculating an intensity of electrical stimulation for the user based on a result of the analyzing;
learning the calculated intensity of electrical stimulation by matching the calculated intensity of electrical stimulation with a corresponding user; and
providing electrical stimulation to the user based on the calculated intensity of electrical stimulation.

13. The method of claim 12, further comprising:
verifying a state of a connection between the intelligent learning terminal and the at least one wireless electrical stimulator when a power is supplied.

14. The method of claim 12, wherein the collecting comprises:
receiving personal information associated with the user from the intelligent learning terminal;
measuring a biometric signal of the user using the at least one wireless electrical stimulator based on a result of the receiving; and
collecting a result of the measuring.

15. The method of claim 12, further comprising:
classifying the result of the analyzing for each user and storing the classified result.

16. The method of claim 12, further comprising:
receiving an intensity of electrical stimulation set by the user as feedback; and
learning the intensity of electrical stimulation set by the user by matching the intensity of electrical stimulation set by the user with the corresponding user.

17. The method of claim 16, further comprising:
storing the intensity of electrical stimulation set by the user.

18. The method claim 12, further comprising:
receiving an intensity of electrical stimulation set by the user as feedback;
storing the intensity of electrical stimulation set by the user;
adjusting a preset intensity of electrical stimulation, based on the intensity of electrical stimulation set by the user;
storing the adjusted intensity of electrical stimulation; and
learning the adjusted intensity of electrical stimulation by matching thing the adjusted intensity of electrical stimulation with the corresponding user.

19. The method of claim 12, further comprising:
recognizing the user based on the result of the analyzing of biometric information associated with the user.

20. The method of claim 12, further comprising:
receiving an intensity of electrical stimulation and a time set by the user; and
adjusting an intensity of electrical stimulation and a time output by the at least one wireless electrical stimulator based on the intensity of electrical stimulation and the time set by the user.

\* \* \* \* \*